US011257301B2

(12) United States Patent
Tominaga

(10) Patent No.: US 11,257,301 B2
(45) Date of Patent: Feb. 22, 2022

(54) IMAGE ANALYSIS APPARATUS, IMAGE ANALYSIS METHOD, AND IMAGE ANALYSIS PROGRAM

(71) Applicant: FUJIFILM Corporation, Tokyo (JP)

(72) Inventor: Shunsuke Tominaga, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 156 days.

(21) Appl. No.: 16/791,496

(22) Filed: Feb. 14, 2020

(65) Prior Publication Data
US 2020/0184192 A1 Jun. 11, 2020

Related U.S. Application Data

(63) Continuation of application No. PCT/JP2018/032613, filed on Sep. 3, 2018.

(30) Foreign Application Priority Data

Sep. 27, 2017 (JP) .............................. JP2017-187086

(51) Int. Cl.
G06K 9/00 (2006.01)
G06V 20/69 (2022.01)
(Continued)

(52) U.S. Cl.
CPC ....... G06V 20/698 (2022.01); G01N 21/6458 (2013.01); G02B 21/16 (2013.01);
(Continued)

(58) Field of Classification Search
CPC ......... G06T 7/0012; G06T 2207/10064; G06T 2207/10056; G06T 2207/30024;
(Continued)

(56) References Cited

U.S. PATENT DOCUMENTS

2007/0121099 A1* 5/2007 Matsumoto ........ G01N 21/6428
356/72
2011/0019898 A1 1/2011 Takagi et al.
(Continued)

FOREIGN PATENT DOCUMENTS

JP 2005227097 A 8/2005
JP 2006018394 A 1/2006
(Continued)

OTHER PUBLICATIONS

International Search Report issued in PCT/JP2018/032613; dated Dec. 4, 2018.
(Continued)

Primary Examiner — Alex Kok S Liew
(74) Attorney, Agent, or Firm — Studebaker & Brackett PC

(57) ABSTRACT

An image analysis apparatus including a processor configured to: acquire a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining; determine whether or not the first region is included in the second region in a superimposed image obtained by superimposing the first fluorescence image and the second fluorescence image and acquire a first determination result for each of the first regions; and determine the type of cell included in the observation target on the basis of the first determination result.

10 Claims, 6 Drawing Sheets

(51) Int. Cl.
  *G01N 21/64* (2006.01)
  *G02B 21/16* (2006.01)
  *G02B 21/36* (2006.01)
  *G06K 9/62* (2022.01)
  *G06V 10/46* (2022.01)

(52) U.S. Cl.
  CPC ......... *G02B 21/365* (2013.01); *G06K 9/6289* (2013.01); *G06V 10/46* (2022.01); *G06V 20/695* (2022.01)

(58) Field of Classification Search
  CPC ... G06T 7/70; G06T 2207/30072; G06T 7/11; G06T 7/187; G06T 2207/20081; G06T 2207/20084; G06T 2207/10024; G06T 7/155; G06T 2207/30096; G06T 2207/10016; G06T 2207/10061; G06T 2207/20036; G06T 2207/20152; G06T 5/50; G06K 9/0014; G06K 9/00147; G06K 9/00127; G06K 9/48; G06K 9/6289; G06K 9/629; G06K 9/00134
  See application file for complete search history.

(56) References Cited

U.S. PATENT DOCUMENTS

| | | | |
|---|---|---|---|
| 2014/0126802 A1* | 5/2014 | Adiga | G06T 5/004 382/133 |
| 2014/0153811 A1* | 6/2014 | Seppo | G06T 7/0012 382/133 |
| 2016/0275673 A1 | 9/2016 | Ichitani et al. | |

FOREIGN PATENT DOCUMENTS

| | | |
|---|---|---|
| JP | 2009122115 A | 6/2009 |
| JP | 2011027542 A | 2/2011 |
| JP | 2017122610 A | 7/2017 |
| WO | 2015145644 A1 | 10/2015 |
| WO | 2016104308 A1 | 6/2016 |

OTHER PUBLICATIONS

International Preliminary Report on Patentability and Written Opinion issued in PCT/JP2018/032613; dated Mar. 31, 2020.

The extended European search report issued by the European Patent Office dated Oct. 15, 2020, which corresponds to European Patent Application No. 18861728.6-1210 and is related to U.S. Appl. No. 16/791,496.

An Office Action; "Notice of Reasons for Refusal," mailed by the Japanese Patent Office dated Mar. 23, 2021, which corresponds to Japanese Patent Application No. 2019-544478 and is related to U.S. Appl. No. 16/791,496; with English language translation.

An Office Action; "Decision of Refusal", mailed by the Japanese Patent Office dated Oct. 26, 2021, which corresponds to Japanese Patent Application No. 2019-544478 and is related to U.S. Appl. No. 16/791,496; with English language translation.

An Office Action mailed by the Korean Intellectual Property Office dated Nov. 29, 2021, which corresponds to Korean Patent Application No. 10-2020-7005655 and is related to U.S. Appl. No. 16/791,496; with English language translation.

* cited by examiner

ND IMAGE
IMAGE ANALYSIS APPARATUS, IMAGE ANALYSIS METHOD, AND IMAGE ANALYSIS PROGRAM

CROSS-REFERENCE TO RELATED APPLICATIONS

This application is a Continuation of PCT International Application No. PCT/JP2018/032613 filed on Sep. 3, 2018, which claims priority under 35 U.S. § 119(a) to Japanese Patent Application No. 2017-187086 filed on Sep. 27, 2017. Each of the above applications is hereby expressly incorporated by reference, in its entirety, into the present application.

BACKGROUND OF THE INVENTION

1. Field of the Invention

The present invention relates to an image analysis apparatus, an image analysis method, and an image analysis program that analyze a fluorescence image of an observation target including a plurality of types of cells.

2. Description of the Related Art

In recent years, a method has been proposed which captures an image of pluripotent stem cells, such as embryonic stem (ES) cells and induced pluripotent stem (iPS) cells, or differentiation-induced cells with, for example, a microscope and checks the characteristics of the captured image to determine the differentiation state of the cells. Pluripotent stem cells, such as ES cells and iPS cells, have the ability to differentiate into cells of various tissues and attract attention as cells applicable to regenerative medicine, drug development, and disease elucidation.

For example, in the fields of regenerative medicine and drug development, an image of cells stained with a fluorescent material is captured and the cells are examined on the basis of a fluorescence image acquired by imaging. Here, examples of the examination of the cells include the enumeration of cells having specific properties, such as undifferentiation, and the evaluation of the morphological characteristics of cells. The examination of the cells is performed by the observer's visual determination. However, in visual examination, there is a variation in the evaluation standard between the observers and the efficiency of examination is low. For this reason, automatic evaluation using an image analysis apparatus is performed.

For example, JP2009-122115A discloses a method which stains cell membranes and cell nuclei with different stainers, acquires different fluorescence images, decides a cell membrane region and a cell nucleus region in each fluorescence image, and determines the observation target to be a cell in a case in which the cell nucleus region is included in the cell membrane region. In addition, JP2006-018394A discloses a method which extracts the contour of a cell nucleus and the contour of a cell in a fluorescence image, determines whether only one cell nucleus or a plurality of cell nuclei are present in the contour of the cell, divides the contour of the cell in a case in which a plurality of cell nuclei are present, and recognizes the cell in which only one nucleus is present in the contour of the cell as a cell.

SUMMARY OF THE INVENTION

However, the method described in JP2009-122115A only determines an observation target to be a cell in a case in which the cell nucleus region is included in the cell membrane region and does not determine the type of cell. Further, the method described in JP2006-018394A determines the number of cell nuclei in the contour of the cell and does not determine the type of cell.

The invention has been made in view of the above-mentioned problems and an object of the invention is to provide a technique that can determine the type of cell included in an observation target.

According to the invention, there is provided an image analysis apparatus comprising: an image acquisition unit that acquires a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining; a first determination unit that determines whether or not the first region is included in the second region in a superimposed image obtained by superimposing the first fluorescence image and the second fluorescence image and acquires a first determination result for each of the first regions; and a second determination unit that determines the type of cell included in the observation target on the basis of the first determination result.

The "first region" is a region included in all of the plurality of types of cells. For example, a cell nucleus of each of the plurality of types of cells can be used as the first region.

For the "second region", for example, the entire region in a cell membrane of a specific cell among the plurality of types of cells can be used as the second region.

The "superimposed image" is an image obtained by superimposing the first fluorescence image and the second fluorescence image such that the corresponding pixels are matched with each other.

In the image analysis apparatus according to the invention, among the plurality of types of cells, cells other than the specific cell may be negative for the second staining.

The term "cell negative for the second staining" means that the cell is not stained by the second staining.

In the image analysis apparatus according to the invention, the first determination unit may extract a contour of the second region from the second fluorescence image and acquire the first determination result on the basis of whether each of the first regions is located within the contour of the corresponding second region in the superimposed image.

In this case, in a case in which it is difficult to acquire the first determination result, the first determination unit may acquire the first determination result on the basis of a percentage at which each of the first regions is located within the contour of the corresponding second region in the superimposed image.

The contour may be extracted before the superimposed image is generated or after the superimposed image is generated.

In the image analysis apparatus according to the invention, the first determination unit may extract a contour of the second region from the second fluorescence image and acquire the first determination result on the basis of a percentage at which each of the first regions is located within the contour of the corresponding second region in the superimposed image.

In the image analysis apparatus according to the invention, the first determination unit may extract a contour of the first region from the first fluorescence image, extract a contour of the second region from the second fluorescence image, and acquire the first determination result on the basis of the contour of the first region and the contour of the second region in the superimposed image.

In this case, the first determination unit may set a first reference point and a second reference point which are adjacent to each other on the contour of the first region and the contour of the second region in the superimposed image, respectively, and acquire the first determination result on the basis of first information indicating a contour direction of the first region at the first reference point, second information indicating a contour direction of the second region at the second reference point, and third information indicating a distance between the first reference point and the second reference point.

According to the invention, there is provided an image analysis method comprising: acquiring a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining; determining whether or not the first region is included in the second region in a superimposed image obtained by superimposing the first fluorescence image and the second fluorescence image and acquires a first determination result for each of the first regions; and determining the type of cell included in the observation target on the basis of the first determination result.

In addition, a program that causes a computer to perform the image analysis method according to the invention may be provided.

According to the invention, there is provided another image analysis apparatus comprising a memory that stores commands to be executed by a computer and a processor that is configured to execute the stored commands. The processor performs a process of acquiring a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining, a process of determining whether or not the first region is included in the second region in a superimposed image obtained by superimposing the first fluorescence image and the second fluorescence image and acquires a first determination result for each of the first regions, and a process of determining the type of cell included in the observation target on the basis of the first determination result.

According to the invention, in the superimposed image obtained by superimposing the first fluorescence image in the first region is stained by the first staining and the second fluorescence image in which the second region of a specific cell is stained by the second staining different from the first staining, it is determined whether or not the first region in the first fluorescence image is included in the second region in the second fluorescence image and the first determination result is acquired. Then, the type of cell included in the observation target is determined on the basis of the first determination result. Here, the first region of each of a plurality of types of cells is stained in the first fluorescence image and the second region of a specific cell is stained in the second fluorescence image. Therefore, for the specific cell, the second region and the first region overlap each other in the superimposed image and the first region is included in the second region. In contrast, since cells other than the specific cell are not stained by the second staining, the first region of the cell other than the specific cell is not included in the second region in the superimposed image. Therefore, according to the invention, it is possible to distinguish a specific type of cell from cells other than the specific type of cell included in the observation target. As a result, it is possible to determine the type of cell included in the observation target.

DESCRIPTION OF THE PREFERRED EMBODIMENTS

Figure 1:
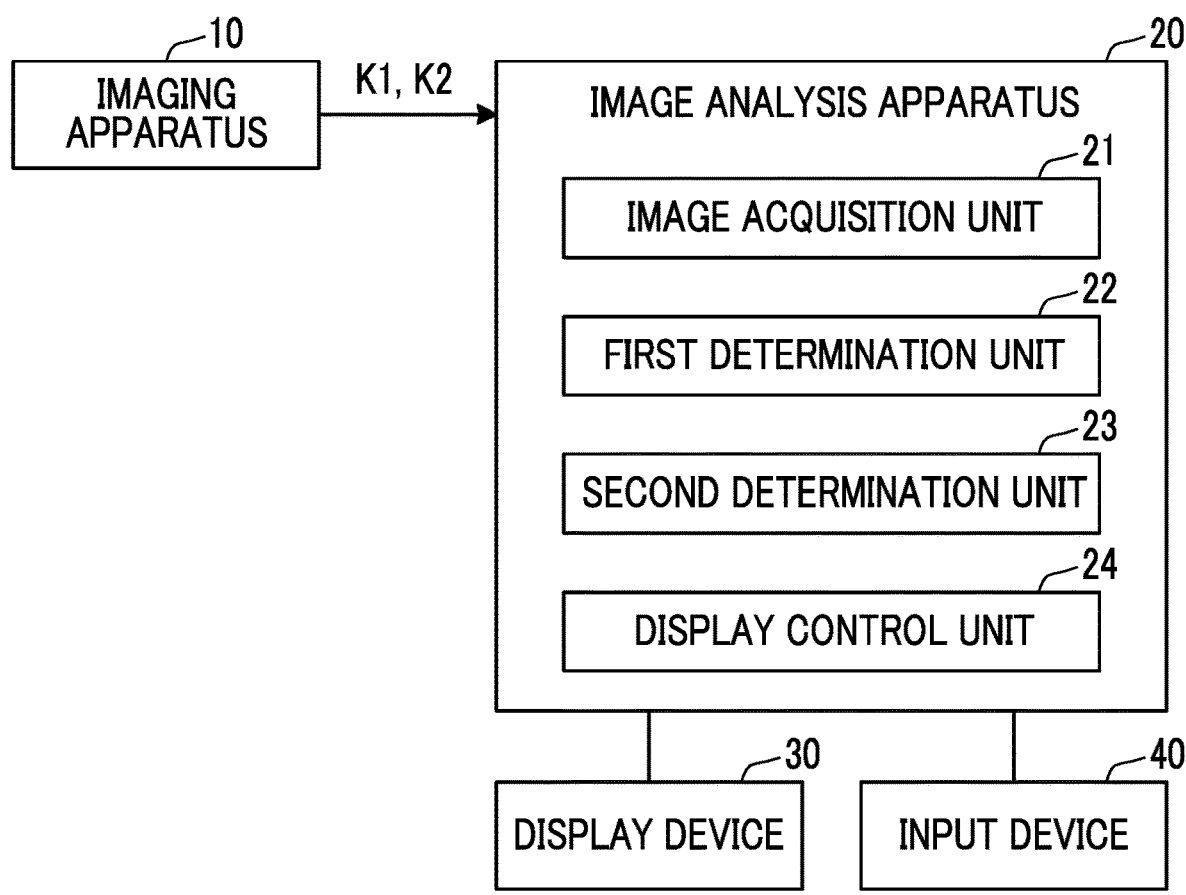
FIG. 1 is a block diagram schematically illustrating the configuration of an image analysis system using an image analysis apparatus according to an embodiment of the invention.

Hereinafter, an image analysis system using an embodiment of an image analysis apparatus according to the invention will be described in detail with reference to the drawings. FIG. 1 is a block diagram schematically illustrating the configuration of the image analysis system according to this embodiment. As illustrated in FIG. 1, the image analysis system according to this embodiment comprises an imaging apparatus 10, an image analysis apparatus 20, a display device 30, and an input device 40.

First, in the image analysis system according to this embodiment, a biological sample including a plurality of types of cells is prepared as an observation target. Examples of the biological sample include pluripotent stem cells, such as cancer cells, iPS cells, and ES cells, nerve cells, skin cells, heart muscle cells, and liver cells differentiation-induced from stem cells, and skin cells, retina cells, heart muscle cells, blood cells, nerve cells, and organ cells extracted from the human body.

In this embodiment, an example in which skin cells cultured using feeder cells are prepared as the biological sample and are evaluated will be described. In addition, the skin cell is a specific cell. Examples of the evaluation are the counting of the number of skin cells and the evaluation of the morphological characteristics of the skin cells. In addition, the skin cells are cultured in a container. The container may be, for example, a petri dish, a multi-well plate, or different wells of one multi-well plate. In this embodiment, first staining is performed for the biological sample to capture a first fluorescence image and then second staining is performed to acquire a second fluorescence image.

A fluorescent material that stains the nuclei of all of the cells contained in the biological sample is used in the first staining. A fluorescent material for keratin staining which stains keratin of the skin cells contained in the biological sample is used in the second staining. Here, the feeder cells are negative for the keratin staining (second staining) and are not stained by the keratin staining. The creation and staining of the biological sample may be performed manually by the user or may be performed automatically using an apparatus including, for example, a mechanism for sucking cells and a robot arm.

The imaging apparatus 10 captures an image of the biological sample subjected to the first staining to acquire a first fluorescence image K1 and then captures an image of the biological sample subjected to the second staining to acquire a second fluorescence image K2. Specifically, a fluorescence microscope apparatus that comprises an imaging element, such as a charge-coupled device (CCD) image sensor or a complementary metal-oxide semiconductor (CMOS) image sensor, and detects the intensity of fluorescence emitted from the biological sample is used as the imaging apparatus 10. An imaging element that is provided with red, green, and blue (RGB) color filters or a monochrome imaging element may be used as the imaging element. The first fluorescence image K1 and the second fluorescence image K2 acquired by the imaging apparatus 10 are input to the image analysis apparatus 20.

As illustrated in FIG. 1, the image analysis apparatus 20 comprises an image acquisition unit 21, a first determination unit 22, a second determination unit 23, and a display control unit 24. The image analysis apparatus 20 is a computer comprising, for example, a central processing unit, a semiconductor memory, and a hard disk drive. An embodiment of an image analysis program according to the invention is installed in the hard disk drive. Then, the central processing unit executes the image analysis program such that the image acquisition unit 21, the first determination unit 22, the second determination unit 23, and the display control unit 24 illustrated in FIG. 1 function. In this embodiment, the functions of each unit are implemented by the image analysis program. However, the invention is not limited thereto. For example, a plurality of integrated circuits (ICs), a processor, an application specific integrated circuit (ASIC), a field-programmable gate array (FPGA), and a memory may be appropriately combined to implement the functions of each unit.

Figure 2:
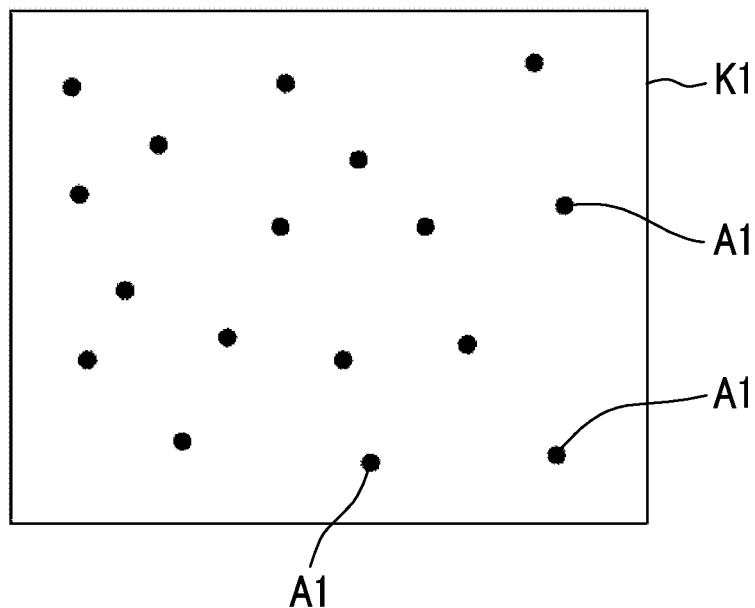
FIG. 2 is a diagram illustrating a first fluorescence image.
Figure 3:
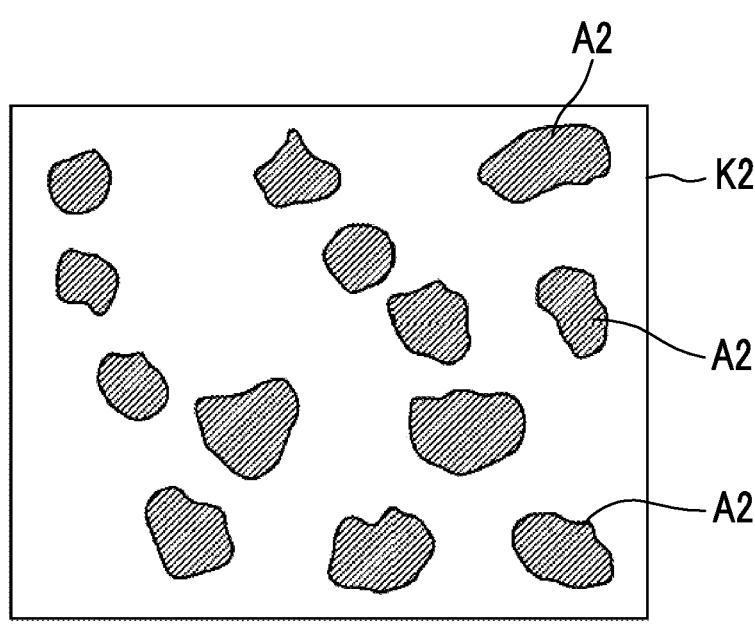
FIG. 3 is a diagram illustrating a second fluorescence image.

The image acquisition unit 21 acquires the first fluorescence image K1 and the second fluorescence image K2 output from the imaging apparatus 10 and stores the acquired images in a storage unit (not illustrated). FIG. 2 is a diagram illustrating the first fluorescence image and FIG. 3 is a diagram illustrating the second fluorescence image. Here, since the nuclei of all of the cells included in the biological sample are stained by the first staining, all of the nuclei of the cells included in the biological sample are stained in the first fluorescence image K1. A region of the cell nucleus included in the first fluorescence image K1 is a first region A1.

In contrast, keratin of the skin cells included in the biological sample is stained by the second staining. Keratin is present in the cell membrane of the skin cell. Therefore, in the second fluorescence image K2, a region in the cell membrane of the skin cell included in the biological sample is stained. A region in the cell membrane of the skin cell included in the second fluorescence image K2 is a second region A2.

Since a fluorescent material for the first staining is different from a fluorescent material for the second staining, the stained first region A1 in the first fluorescence image K1 and the stained second region A2 in the second fluorescence image K2 emit different fluorescent colors. In order to show this state, the stained first region A1 in the first fluorescence image K1 is blacked out in FIG. 2 and the stained second region A2 in the second fluorescence image K2 is hatched in FIG. 3.

The first determination unit 22 determines whether or not the first region A1 is included in the second region A2 and acquires a first determination result for each of the first regions A1. For this operation, the first determination unit 22 extracts the contour of the stained second region A2, that is, the region of the cell membrane of the skin cell from the second fluorescence image K2. For example, a method using a differential filter can be used as a method for extracting the contour. In addition, the contour may be extracted by a method that performs a binarization process for the second fluorescence image K2 to acquire a binarized image and traces a boundary line between the regions in the binarized image. Further, any method, such as adaptive binarization or Otsu's Binarization, may be used as the binarization process.

Figure 4:
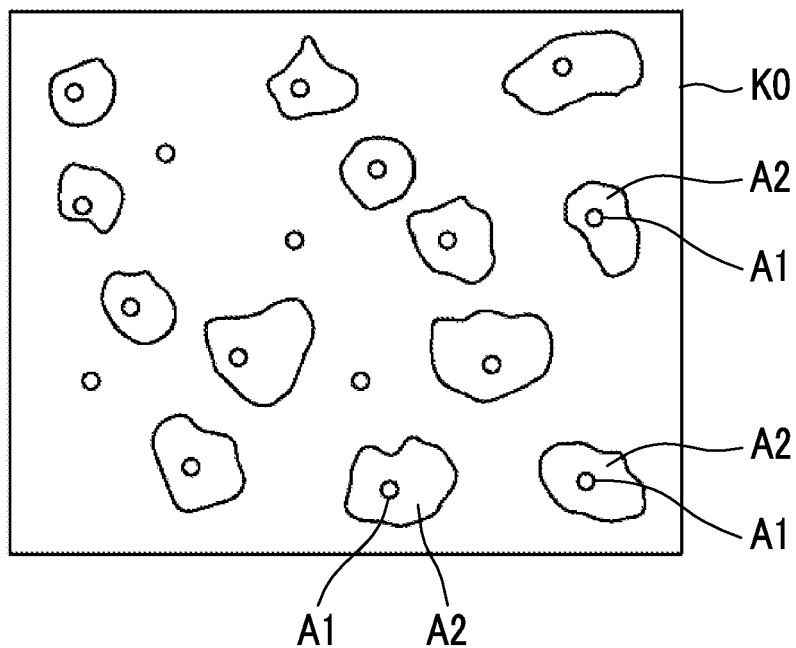
FIG. 4 is a diagram illustrating a superimposed image.

The first determination unit 22 superimposes the second fluorescence image K2, from which the contour of the second region A2 has been extracted, and the first fluorescence image K1 to generate a superimposed image K0. FIG. 4 is a diagram illustrating the superimposed image generated in this embodiment. In the superimposed image K0 illustrated in FIG. 4, the filling of the first region A1 and an oblique line to the second region A2 are omitted. The first determination unit 22 determines whether or not each of the first regions A1 is included in the corresponding second region A2 on the basis of whether or not each of the first regions A1 included in the superimposed image K0 is located within the contour of the second region A2 and acquires the first determination result.

Figure 5:
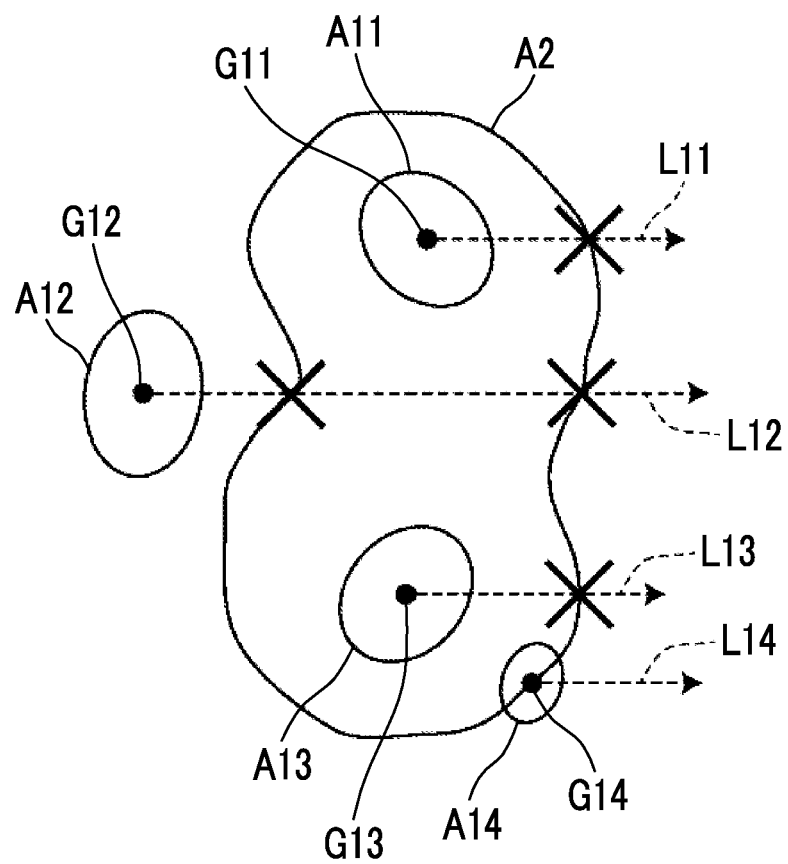
FIG. 5 is a diagram illustrating the inclusion of a first region in a second region.

FIG. 5 is a diagram illustrating the inclusion of the first region in the second region. In FIG. 5, four first regions A11, A12, A13, and A14 and one second region A2 corresponding to the four first regions are illustrated. The first determination unit 22 detects the centers of gravity G11, G12, G13, and G14 of the first regions A11, A12, A13, and A14. Then, the first determination unit 22 draws half lines L11, L12, L13, and L14 from the centers of gravity G11, G12, G13, and G14 in a predetermined direction in the superimposed image K0 and detects the number of intersection points between the half lines L11, L12, L13, and L14 and the contour of the second region A2. Then, the first determination unit 22 determines that the first region A1 is located within the contour of the second region A2 in a case in which the number of intersection points is odd and determines that the first region A1 is located out of the contour of the second region A2 in a case in which the number of intersection points is even. For example, for the first regions A11 and A13, since each of the half lines L11 and L13 intersects the second region A2 at one point, the first regions A11 and A13 are located within the contour of the second region A2. Therefore, it is determined that the first regions A11 and A13 are included in the second region A2. For the first region A12, since the half line L12 intersects the second region A2 at two points, the first region A12 is located out of the contour of the second region A2. Therefore, it is determined that the first region A12 is not included in the second region A2. For the first region A14, it is difficult to clearly determine whether or not the half line L14 intersects the second region A2. It is difficult to perform the determination for the first region A14. That is, it is determined that the determination for the first region A14 is impossible.

Figure 6:
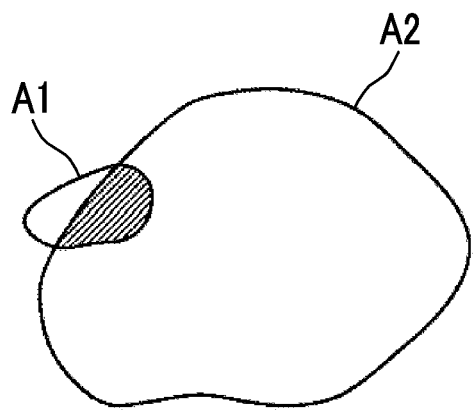
FIG. 6 is a diagram illustrating the calculation of a percentage at which the first region is located within the contour of the second region.

The first determination unit 22 calculates the percentage at which the first region A1 for which the determination is impossible is located within the contour of the second region A2. FIG. 6 is a diagram for explaining the calculation of the percentage at which the first region is located within the contour of the second region. The first determination unit 22 calculates the percentage at which the first region A1 is located within the contour of the second region A2 by calculating the area S11 of the entire first region A1 and the area S12 of a portion of the first region A1 which is included in the contour of the second region A2 as represented by hatching in FIG. 6 and calculating a value obtained by dividing the latter by the former, that is, S12/S11. The first determination unit 22 determines whether or not the calculated percentage is equal to or greater than a predetermined threshold value Th1. In a case in which the percentage is equal to or greater than the threshold value Th1, the first determination unit 22 determines that the first region A1 is included in the second region A2. As the threshold value Th1, a relatively high value (for example, 80%) can be used in order to prevent erroneous detection. On the other hand, in a case in which the calculated percentage is less than the threshold value Th1, the first determination unit 22 determines that the first region A1 is not included in the second region A2.

Figure 7:
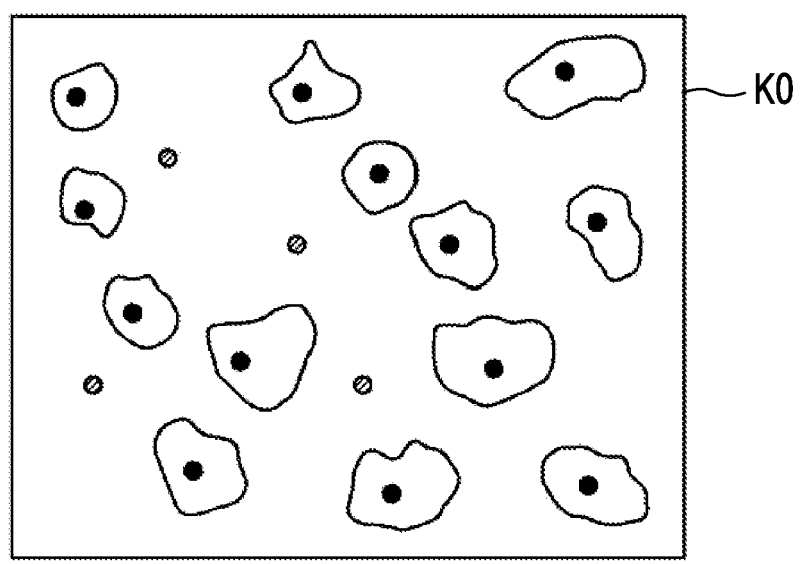
FIG. 7 is a diagram illustrating a superimposed image in which a marker is given.

The second determination unit 23 determines the type of cell included in the observation target on the basis of the first determination result of the first determination unit 22. Specifically, the second determination unit 23 determines the cell in which the first region A1 is included in the second region A2 to be a skin cell and determines the cell in which the first region A1 is not included in the second region A2 to be a feeder cell. In addition, the second determination unit 23 may give different markers to the determined cell types in the superimposed image K0. For example, markers of different colors may be given to the determined cell types. FIG. 7 is a diagram illustrating a superimposed image to which markers are given. In FIG. 7, the markers of different colors are given to the nucleus of the skin cell and the nucleus of the feeder cell. For example, the nucleus of the skin cell is filled with a color and the nucleus of the feeder cell is hatched. In addition, markers with different shapes may be given instead of the markers of different colors.

The display control unit 24 displays, for example, the first fluorescence image K1, the second fluorescence image K2, and the superimposed image K0 on the display device 30.

The display device 30 displays, for example, the first fluorescence image K1, the second fluorescence image K2, and the superimposed image K0 in response to a command from the display control unit 24 and comprises, for example, a liquid crystal display. In addition, the display device 30 may be configured by a touch panel and may also be used as the input device 40.

The input device 40 comprises, for example, a mouse and a keyboard and receives various settings input by the user.

Figure 8:
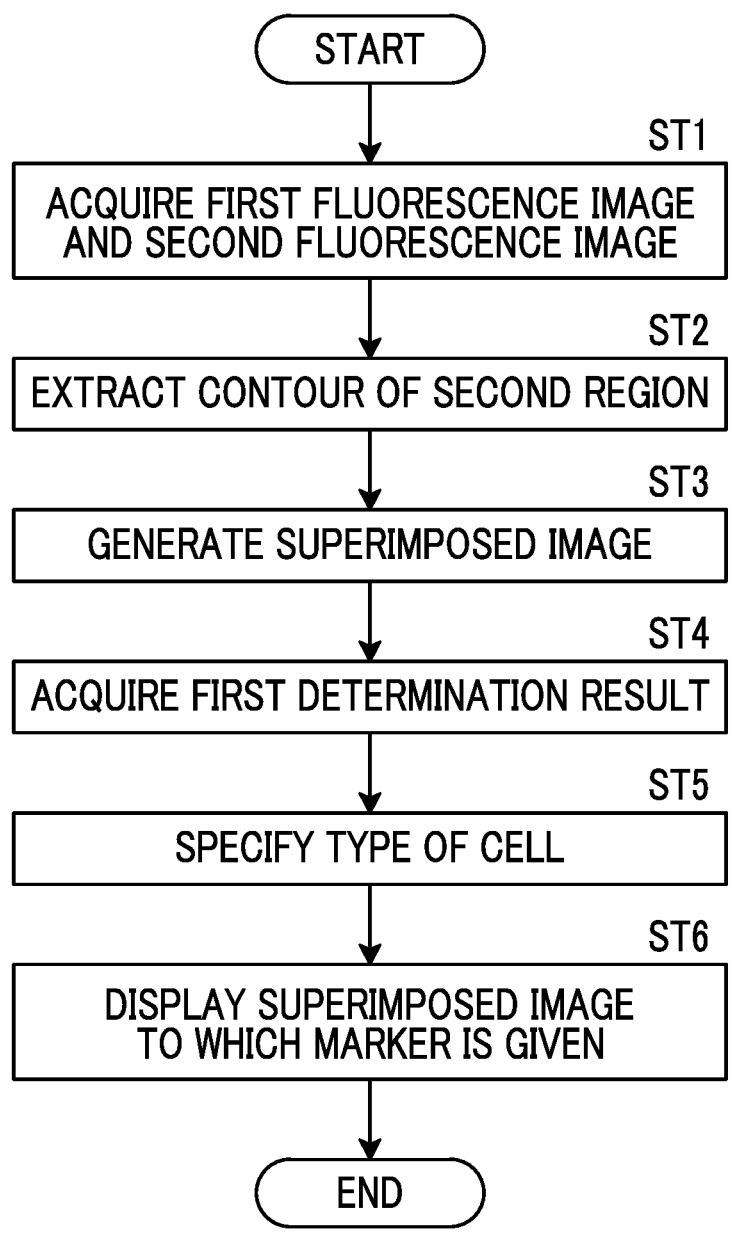
FIG. 8 is a flowchart illustrating a process performed in this embodiment.

Next, a process performed in this embodiment will be described. FIG. 8 is a diagram illustrating the process performed in this embodiment. First, the image acquisition unit 21 acquires the first fluorescence image K1 and the second fluorescence image K2 acquired by capturing the images of the biological sample using the imaging apparatus 10 (Step ST1). Then, the first determination unit 22 extracts the contour of the second region A2 included in the second fluorescence image K2 (Step ST2) and superimposes the second fluorescence image K2 from which the contour has been extracted and the first fluorescence image K1 to generate the superimposed image K0 (Step ST3). In addition, the first determination unit 22 determines whether or not each of the first regions A1 included in the superimposed image K0 is included in the corresponding second region A2 and acquires the first determination result (Step ST4). Then, the second determination unit 23 specifies the type of cell included in the observation target on the basis of the first determination result (Step ST5). Then, the display control unit 24 displays the superimposed image K0, to which the marker corresponding to the cell type have been given, on the display device 30 (Step ST6). Then, the process ends.

As such, in this embodiment, in the superimposed image K0 obtained by superimposing the first fluorescence image K1 and the second fluorescence image K2, it is determined whether or not the first region A1 of the first fluorescence image K1 is included in the second region A2 of the second fluorescence image K2 and the first determination result is acquired. Then, the type of cell included in the observation target is determined on the basis of the first determination result. Here, the first regions A1 of a plurality of types of cells, that is, the cell nuclei are stained in the first fluorescence image K1 and the second region A2 of a specific cell, that is, a skin cell is stained in the second fluorescence image K2. Therefore, for the skin cell, the second region A2 and the first region A1 overlap each other in the superimposed image K0 and the first region A1 is included in the second region A2. In contrast, since cells other than the skin cell, that is, feeder cells are not stained by the second staining, the first region A1 of the feeder cell is not included in the second region A2 in the superimposed image K0. Therefore, according to the invention, it is possible to distinguish a specific type of cell included in the observation target, that is, a skin cell from a cell other than the specific type of cell, that is, a feeder cell. As a result, it is possible to determine the type of cell included in the observation target.

Figure 9:
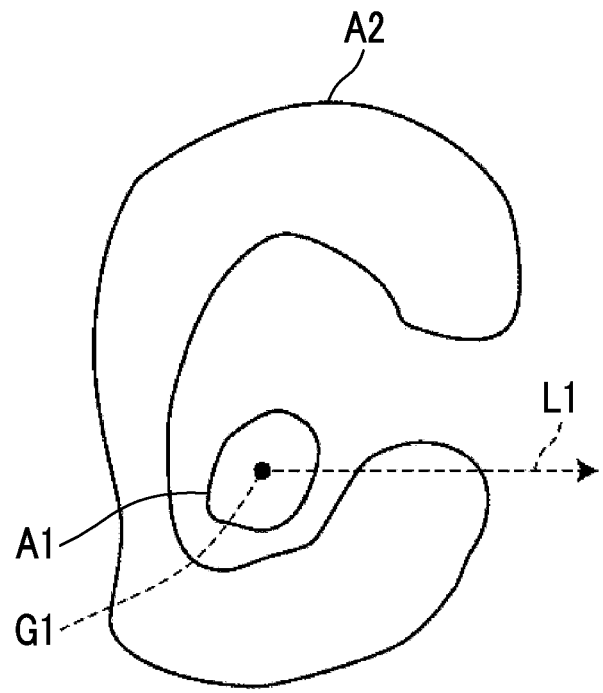
FIG. 9 is a diagram illustrating an example in which the first region is determined not to be included in the second region.

In the above-described embodiment, the first determination unit 22 determines whether or not the first region A1 is included in the second region A2. However, in some cases, for example, it is difficult to determine whether or not the first region A1 is included in the second region A2 because it is difficult to clearly extract the contour of the second region A2. For example, as illustrated in FIG. 9, it is considered that the first region A1 is included in the second region A2. However, since the number of intersection points between the half line L1 drawn from the center of gravity G1 of the first region A1 and the contour of the second region A2 is 2, it is determined that the first region A1 is not included in the second region A2.

Figure 10:
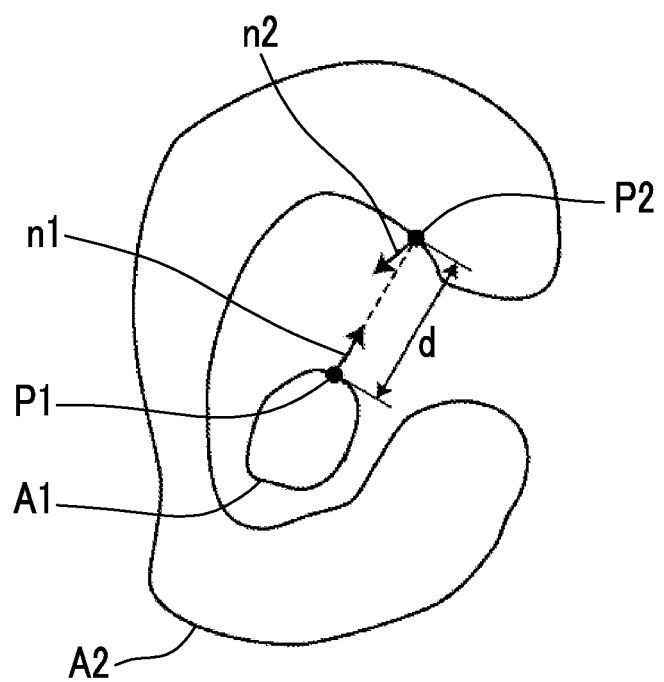
FIG. 10 is a diagram illustrating the acquisition of a first determination result by another embodiment.

Therefore, the first determination unit 22 may acquire the first determination result on the basis of the contour of the first region A1 and the contour of the second region A2. Next, another embodiment will be described. FIG. 10 is a diagram illustrating the acquisition of a first determination result by another embodiment. First, the first determination unit 22 sets a first reference point P1 on the contour of the first region A1 and sets an outward unit normal vector n1 at the first reference point P1. The unit normal vector n1 is first information indicating the contour direction of the first region A1 at the first reference point P1. The first determination unit 22 sets an intersection point of an extension line of the unit normal vector n1 and the contour of the second region A2 as a second reference point P2. In a case in which there are a plurality of intersection points, an intersection point closest to the first reference point P1 is set as the second reference point P2. Further, the first determination unit 22 sets a unit normal vector n2 that faces the first reference point P1 at the second reference point P2. The unit normal vector n2 is second information indicating the contour direction of the second region A2 at the second reference point P2. In addition, the first determination unit 22 calculates a distance d (for example, the Euclidean distance) between the first reference point P1 and the second reference point P2. The distance d is third information indicating the distance between the first reference point P1 and the second reference point P2.

Then, the first determination unit 22 calculates the similarity between the contour of the first region A1 and the contour of the second region A2 on the basis of an evaluation value of the similarity between the contour direction of the first region A1 and the contour direction of the second region A2 and an evaluation value of the distance between the contour of the first region A1 and the contour of the second region A2. Specifically, the first determination unit 22 calculates the absolute value of the inner product of the unit normal vectors n1 and n2 as the evaluation value of the similarity between the contour direction of the first region A1 and the contour direction of the second region A2. In addition, for the distance d between the first reference point P1 and the second reference point P2, a value of 1/(1+d) is calculated as the evaluation value of the distance between the contour of the first region A1 and the contour of the second region A2. The evaluation value of the similarity between the contour directions becomes larger as the directions of the unit normal vectors n1 and n2 become closer to parallel. The evaluation value of the distance becomes larger as the distance d becomes shorter. Then, the first determination unit 22 performs weighted addition for the evaluation value of the similarity and the evaluation value of the distance to calculate the similarity between the contour of the first region A1 and the contour of the second region A2. Specifically, the similarity S(P1) between the contour of the first region A1 and the contour of the second region A2 is calculated by the following Expression (1).

[Expression 1]

$$S(P_1) = w_1 \|\vec{n}_1 \cdot \vec{n}_2\| + w_2 \frac{1}{1+d} \quad (1)$$

In Expression (1), w1 and w2 are weight coefficients. The first determination unit 22 determines whether or not the similarity S(P1) is equal to or greater than a predetermined threshold value Th2. In a case in which the similarity S(P1) is equal to or greater than the threshold value Th2, the first determination unit 22 determines that the first region A1 is included in the second region A2 with respect to the set first reference point P1. The first determination unit 22 calculates the similarity S(P1) while changing the position of the first reference point P1 over the entire circumference of the contour of the first region A1 and determines whether or not the first region A1 is included in the second region A2 with respect to the set first reference point P1. Then, in a case in which the percentage at which the first region A1 is determined to be included in the second region A2 for all of the first reference points P1 is equal to or greater than a predetermined threshold value Th3, the first determination unit 22 determines that the first region A1 is included in the second region A2.

As such, even in a case in which it is difficult to determine whether or not the first region A1 is included in the second region A2, the configuration based on the intersection point between the half line drawn from the center of gravity of the first region A1 and the contour of the second region A2 makes it possible to determine whether or not the first region A1 is included in the second region A2 on the basis of the contour of the first region A1 and the contour of the second region A2.

In the above-described embodiment, as the biological sample to be observed, the skin cells cultured using the feeder cells are used to determine whether or not the cells contained in the biological sample are the feeder cells or the skin cells. However, the invention is not limited thereto. In this embodiment, it is possible to determine the type of cell for a biological sample including cells that are negative for the second staining and cells that are positive for the second staining. For example, this embodiment can also be applied to a case in which pluripotent stem cells, such as ES cells and iPS cells, or differentiation-induced cells are used as the biological samples and the differentiation state of the cells is evaluated. In this case, a fluorescent material that stains the nuclei of cells is used for the first staining and differentiation markers, such as Lin28, TRA-1-60, SSEA-4, and SSEA-1, are used for the second staining to stain the cytoplasm and/or the cell membrane. Undifferentiated cells are negative for the second staining. Therefore, in this embodiment, the first staining and the second staining can be performed to distinguish differentiated cells and undifferentiated cells.

In the above-described embodiment, after the contour of the second region A2 is extracted from the second fluorescence image K2, the superimposed image K0 is generated. However, after the first fluorescence image K1 and the second fluorescence image K2 are superimposed, the contour of the second region A2 included in the second fluorescence image K2 may be extracted and the superimposed image K0 may be generated.

In the above-described embodiment, after the contour of the second region A2 is extracted from the second fluorescence image K2, the superimposed image K0 is generated. However, the contour of the second region A2 may not be extracted and the first fluorescence image K1 and the second fluorescence image K2 may be superimposed to generate the superimposed image K0.

In the above-described embodiment, the first determination unit 22 determines whether or not the first region A1 is located within the contour of the second region A2 and determines whether or not the first region A1 is included in the second region A2 on the basis of the percentage at which the first region A1 is located within the contour of the second region A2 in a case in which it is difficult to perform the determination, that is, in a case in which the determination is impossible. However, it may be determined whether or not the first region A1 is included in the second region A2 on the basis of the percentage at which the first region A1 is located within the contour of the second region A2, without determining whether or not the first region A1 is located within the contour of the second region A2.

EXPLANATION OF REFERENCES

10: imaging apparatus
20: image analysis apparatus
21: image acquisition unit
22: first determination unit
23: second determination unit
24: display control unit 30: display device
40: input device
A1, A11, A12, A13, A14: first region
A2: second region
d: distance between first reference point and second reference point
G1, G11, G12, G13, G14: center of gravity
K0: superimposed image
K1: first fluorescence image
K2: second fluorescence image
L1, L11, L12, L13, L14: half line
n1, n2: unit normal vector
P1: first reference point
P2: second reference point

What is claimed is:

1. An image analysis apparatus comprising:
a processor configured to:
acquire a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining;
determine whether or not the first region is included in the second region in a superimposed image obtained by superimposing the first fluorescence image and the second fluorescence image and acquire a first determination result for each of the first regions; and
determine the type of cell included in the observation target on the basis of the first determination result, wherein
the processor is configured to
extract a contour of the first region from the first fluorescence image, extract a contour of the second region from the second fluorescence image, and acquire the first determination result on the basis of the contour of the first region and the contour of the second region in the superimposed image, and
set a first reference point and a second reference point which are adjacent to each other on the contour of the first region and the contour of the second region in the superimposed image, respectively, and acquire the first determination result on the basis of first information indicating a contour direction of the first region at the first reference point, second information indicating a contour direction of the second region at the second reference point, and third information indicating a distance between the first reference point and the second reference point.

2. The image analysis apparatus according to claim 1, wherein,
among the plurality of types of cells, cells other than the specific cell are negative for the second staining.

3. The image analysis apparatus according to claim 1, wherein
the processor is configured to extract a contour of the second region from the second fluorescence image and acquire the first determination result on the basis of whether each of the first regions is located within the contour of the corresponding second region in the superimposed image.

4. The image analysis apparatus according to claim 2, wherein
the processor is configured to extract a contour of the second region from the second fluorescence image and acquire the first determination result on the basis of whether each of the first regions is located within the contour of the corresponding second region in the superimposed image.

5. The image analysis apparatus according to claim 3, wherein
the processor is further configured to, in a case in which it is difficult to acquire the first determination result, acquire the first determination result on the basis of a percentage at which each of the first regions is located within the contour of the corresponding second region in the superimposed image.

6. The image analysis apparatus according to claim 4, wherein
the processor is further configured to, in a case in which it is difficult to acquire the first determination result, acquire the first determination result on the basis of a percentage at which each of the first regions is located within the contour of the corresponding second region in the superimposed image.

7. The image analysis apparatus according to claim 1, wherein
the processor is further configured to extract a contour of the second region from the second fluorescence image and acquire the first determination result on the basis of a percentage at which each of the first regions is located within the contour of the corresponding second region in the superimposed image.

8. The image analysis apparatus according to claim 2, wherein
the processor is further configured to extract a contour of the second region from the second fluorescence image and acquire the first determination result on the basis of a percentage at which each of the first regions is located within the contour of the corresponding second region in the superimposed image.

9. An image analysis method comprising:
acquiring a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining;
determining whether or not the first region is included in the second region in a superimposed image obtained by superimposing the first fluorescence image and the second fluorescence image and acquires a first determination result for each of the first regions; and
determining the type of cell included in the observation target on the basis of the first determination result, wherein
the image analysis method further comprises
extracting a contour of the first region from the first fluorescence image, extracting a contour of the second region from the second fluorescence image, and acquiring the first determination result on the basis of the contour of the first region and the contour of the second region in the superimposed image, and
setting a first reference point and a second reference point which are adjacent to each other on the contour of the first region and the contour of the second region in the superimposed image, respectively, and acquiring the first determination result on the basis of first information indicating a contour direction of the first region at the first reference point, second information indicating a contour direction of the second region at the second reference point, and third information indicating a distance between the first reference point and the second reference point.

10. A non-transitory computer readable recording medium storing an image analysis program that causes a computer to perform a process comprising:

acquiring a first fluorescence image indicating an observation target including a plurality of types of cells, each of which has a first region stained by first staining, and a second fluorescence image indicating the observation target in which a second region of a specific cell among the plurality of types of cells is stained by second staining different from the first staining;

determining whether or not the first region is included in the second region in a superimposed image obtained by superimposing the first fluorescence image and the second fluorescence image and acquires a first determination result for each of the first regions; and determining the type of cell included in the observation target on the basis of the first determination result, wherein the image analysis program causes the computer to further perform processes of:

extracting a contour of the first region from the first fluorescence image, extracting a contour of the second region from the second fluorescence image, acquiring the first determination result on the basis of the contour of the first region and the contour of the second region in the superimposed image, and setting a first reference point and a second reference point which are adjacent to each other on the contour of the first region and the contour of the second region in the superimposed image, respectively, and acquiring the first determination result on the basis of first information indicating a contour direction of the first region at the first reference point, second information indicating a contour direction of the second region at the second reference point, and third information indicating a distance between the first reference point and the second reference point.

* * * * *